US009096422B2

(12) United States Patent
Hajati

(10) Patent No.: US 9,096,422 B2
(45) Date of Patent: Aug. 4, 2015

(54) PIEZOELECTRIC ARRAY EMPLOYING INTEGRATED MEMS SWITCHES

(71) Applicant: Arman Hajati, Santa Clara, CA (US)

(72) Inventor: Arman Hajati, Santa Clara, CA (US)

(73) Assignee: FUJIFILM DIMATIX, INC., Lebanon, NH (US)

( * ) Notice: Subject to any disclaimer, the term of this patent is extended or adjusted under 35 U.S.C. 154(b) by 283 days.

(21) Appl. No.: 13/768,820

(22) Filed: Feb. 15, 2013

(65) Prior Publication Data

US 2014/0232241 A1 Aug. 21, 2014

(51) Int. Cl.
H01L 41/08 (2006.01)
A61B 8/00 (2006.01)
B81B 7/00 (2006.01)
B81B 7/02 (2006.01)
H01L 41/09 (2006.01)

(52) U.S. Cl.
CPC . B81B 7/008 (2013.01); B81B 7/02 (2013.01); H01L 41/0825 (2013.01); H01L 41/0973 (2013.01)

(58) Field of Classification Search
CPC .... B06B 1/0622; B06B 1/0629; B06B 1/067; B06B 1/0603; H04R 17/00; G10K 11/02; G10K 11/28; G10K 9/122
USPC .................................. 310/322, 334; 600/447
See application file for complete search history.

(56) References Cited

U.S. PATENT DOCUMENTS

| | | | |
|---|---|---|---|
| 6,500,120 B1 | 12/2002 | Anthony | |
| 6,552,841 B1 | 4/2003 | Lasser et al. | |
| 8,008,842 B2 * | 8/2011 | Jiang et al. | 310/334 |
| 2005/0096546 A1 * | 5/2005 | Hazard et al. | 600/447 |
| 2005/0169107 A1 * | 8/2005 | Thomenius et al. | 367/155 |
| 2005/0237858 A1 | 10/2005 | Thomenius et al. | |
| 2007/0188049 A1 * | 8/2007 | Song et al. | 310/322 |
| 2008/0146938 A1 * | 6/2008 | Hazard et al. | 600/462 |
| 2009/0182233 A1 | 7/2009 | Wodnicki | |
| 2010/0141093 A1 | 6/2010 | Fraser et al. | |
| 2010/0207489 A1 | 8/2010 | Huang | |
| 2011/0021923 A1 * | 1/2011 | Daft et al. | 600/459 |
| 2011/0074248 A1 | 3/2011 | Hishinuma | |
| 2013/0303917 A1 * | 11/2013 | Ona et al. | 600/459 |
| 2014/0031694 A1 * | 1/2014 | Solek | 600/459 |
| 2014/0184027 A1 * | 7/2014 | Rice et al. | 310/348 |
| 2014/0187960 A1 * | 7/2014 | Corl | 600/466 |

OTHER PUBLICATIONS

"PCT, International Search Report and The Written Opinion of the International Searching Authority for International Patent Application No. PCT/US2014/013858", (May 15, 2014), Whole Document.

* cited by examiner

Primary Examiner — Thomas Dougherty
(74) Attorney, Agent, or Firm — Blakely, Sokoloff, Taylor & Zafman LLP

(57) ABSTRACT

Switchable micromachined transducer arrays are described where a MicroElectroMechanical Systems (MEMS) switch, or relay, is monolithically integrated with a transducer element. In embodiments, the MEMS switch is implemented in the same substrate as the transducer array to implement one or more logic, addressing, or transducer control function. In embodiments, each transducer element of an array is a piezoelectric element coupled to at least one MEMS switch to provide element-level addressing within the array. In certain embodiments the same piezoelectric material employed in the transducer is utilized in the MEMS switch.

23 Claims, 14 Drawing Sheets

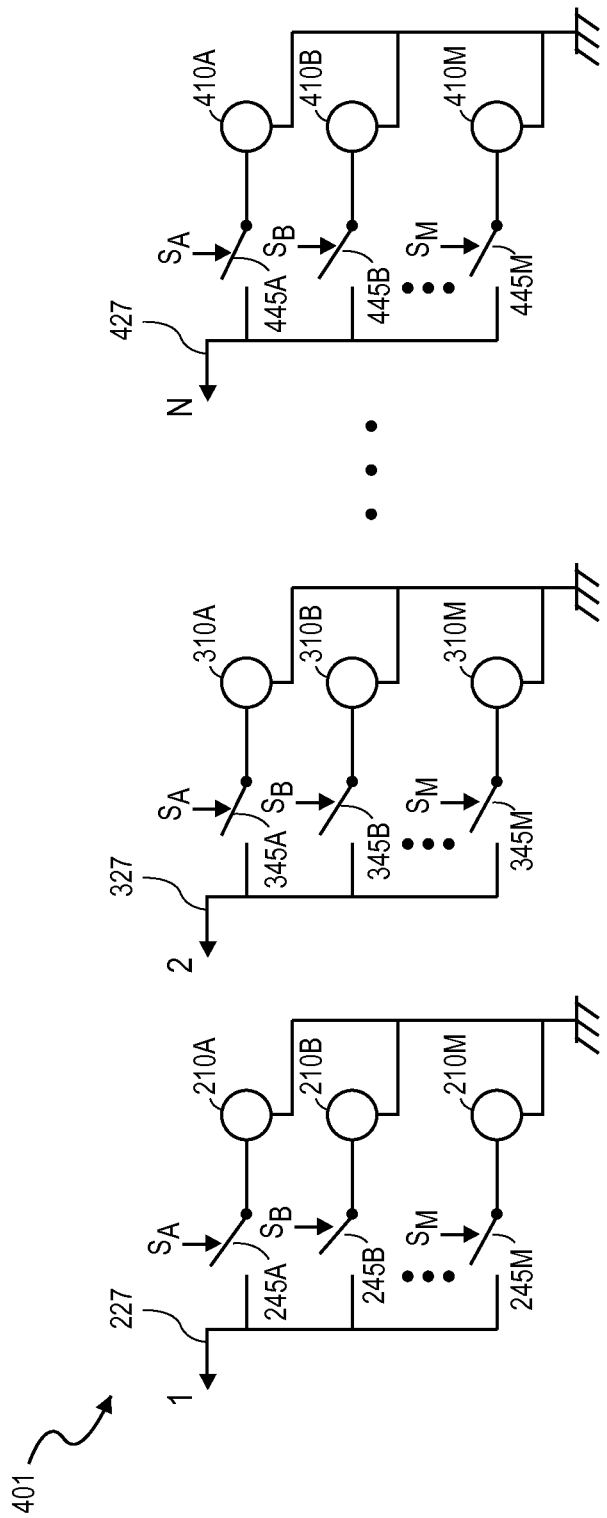

PIEZOELECTRIC ARRAY EMPLOYING INTEGRATED MEMS SWITCHES

TECHNICAL FIELD

Embodiments of the invention generally relate to arrays of piezoelectric transducers, and more specifically pertain to Microelectromechanical (MEM) switched 2D piezoelectric transducers arrays.

BACKGROUND

Transducer arrays are utilized in many applications. Print heads for inkjet or 3D printers are one widespread application, for example. Transducer arrays also find application in ultrasonic imaging. Transducer arrays often employ capacitive or piezoelectric transducer elements. Generally, a piezoelectric transducer element includes a piezoelectric membrane capable of mechanical deflection of the membrane in response to a time-varying driving voltage. For print heads, the membrane is driven to expel ink or other fluid in a controllable manner, for ultrasonic piezoelectric transducer devices the membrane is driven to generate a high frequency pressure wave in a propagation medium (e.g., air, water, or body tissue) in contact with an exposed outer surface of the transducer element. This high frequency pressure wave can propagate into other media. The same piezoelectric membrane can also receive reflected pressure waves from the propagation media and convert the received pressure waves into electrical signals. The electrical signals can be processed in conjunction with the driving voltage signals to obtain information on variations of density or elastic modulus in the propagation media.

While many transducer devices that use piezoelectric membranes may be formed by mechanically dicing a bulk piezoelectric material or by injection molding a carrier material infused with piezoelectric ceramic crystals, devices can be advantageously fabricated inexpensively to exceedingly high dimensional tolerances using various micromachining techniques (e.g., material deposition, lithographic patterning, feature formation by etching, etc.), commonly referred to a piezoelectric micromachined transducers (pMUT), and more specifically a piezoelectric micromachined ultrasonic transducer (pMUT) when configured for ultrasonic transduction.

One-dimensional (1D) pMUT arrays are commonly employed where n channels are provided and each of the n channels addresses m pMUT devices as a single population. During operation of the array, a given one of the n channels is in a drive or sense mode with potentials being applied or sensed from a channel coupled in electrical parallel to m pMUT devices. Signals to/from the n channels of the 1D array may then be achieved through a multiplexing technique, such as time delayed scanning.

FIG. 1A illustrates a 1D array 100 having a plurality of channels 110, 120, 130, 140 disposed over an area defined by a first dimension, x and a second dimension y, of a substrate 101. Each of the channels (e.g., 110) is electrically addressable as one of n channels independently from any other drive/sense channels (e.g., 120 or 130) with the drive/sense channel addressing each of the elements 110A, 110B . . . 110L. A reference (e.g., ground) electrode rail is also typically found in a plane below the drive/sense channel routing. The drive/sense channels 110, 120 represent a repeating cell in the 1D array 100 with the first drive/sense channel 110 coupled to a first bus 127 and the adjacent drive/sense channel 120 coupled a second bus 128 to form a interdigitated finger structure. The drive/sense channels 130, 140 repeat the interdigitated unit structure with additional cells forming a 1D electrode array of arbitrary size (e.g., 128 channels, 256 channels, etc.).

Fully addressable two-dimensional (2D) piezoelectric arrays would offer a number of technical advantages over 1D arrays. For example, in the context of ultrasonic imagers, three-dimensional (3D) imaging becomes possible. Enhanced functionality stemming from the additional degree of freedom provided by transducer element-level addressing is also advantageous in printing and a myriad of other contexts. However, addressing individual pMUT devices within a 2D array is technically challenging because the sheer number of channels scales rapidly, requiring complex device interconnection and multi-layered flex assemblies between the arrayed pMUT device (e.g., print head, ultrasonic transducer head, etc.) and the electrical control/sampling circuitry, often implemented in CMOS, off the transducer substrate. As an example of such an architecture, FIG. 1B is a cross-sectional side view of the 1D pMUT array 100, disposed on the substrate 101 and coupled by a flex cable extending off the substrate 101 to an ASIC (CMOS) controller 112. With such an architecture, increasing complexity in the pMUT device array and/or control of the transducer elements incurs significant overhead off the array substrate.

SUMMARY OF DESCRIPTION

Switched micromachined transducer arrays are described herein. In an embodiment, a MicroElectroMechanical Systems (MEMS) switch, or relay, is integrated with a transducer element. The MEMS switch may be a series switch, as in a pass gate for example, or a shunt switch. In embodiments, the MEMS switch is implemented in the same substrate as the transducer array, or in a separate substrate bonded to that of the transducer array, to implement one or more logic gate, shift register, transducer control, or transducer element addressing function rather than relegating all such functions to CMOS ASICs coupled to the transducer array substrate through interconnects. In embodiments, each transducer element of an array is a piezoelectric element coupled to at least one MEMS switch to provide element-level addressing within the array. In certain embodiments, a MEMS switch employs the same piezoelectric material employed in the transducer. In other embodiments, the MEMS switch is capacitive, electrostatic or electromagnetic while the transducer is capacitive or piezoelectric.

A switch controller coupled to one or more MEMS switches actuates one or more of the MEMS switches to couple a sense and/or drive circuit to a given piezoelectric transducer element, or subset of elements in array, at a given time. In embodiments, sample and hold circuitry may be further coupled to a transducer element or plurality of elements corresponding to a given channel and may utilize the MEMS switch to achieve a sample and hold functionality suitable for pre-conditioning an output signal upstream of an ASIC. In one such embodiment, the sample and hold circuitry includes a capacitor implemented in the same substrate as the transducer array.

In embodiments, a micromachined transducer array is a 2D array where MEMS switches coupled to individual transducer elements are employed to access a particular row of transducer elements while a column sense/drive circuitry is coupled to a particular column of the transducer elements at a given time to provide multiplexing at the element-level. In such embodiments, a raster scanning of the micromachined transducer array may be achieved by scanning through n columns of transducer elements in a 2D array while scanning through m rows of MEMS switches to couple one transducer element to sense and/or drive circuitry at a given time. As such, interconnects between a transducer substrate circuitry to control and drive/sense circuitry implemented in CMOS on a separate substrate can be reduced from m-by-n channel interconnects (or $n^2$ in the case of a square array) to m+n channel interconnects (or 2n in the case of a square array). In further embodiments, a larger number of MEMS switches may be utilized to provide more complex logic-gate functions implemented on the same substrate as the transducer array without complex fabrication techniques. Such logic-gate functions may implement, for example, an m-channel demultiplexing row selector to connect one of m transducer rows to an input voltage based on a select signal, or may implement a pass gates controllable by a shift register enabling addition, accumulation, delayed sampling, etc. of one or more transducer elements in an array.

In embodiments, the MEMS switchable PMUT array is specifically a MEMS switchable piezoelectric micromachined ultrasonic transducers (pMUT) array. Further embodiments include ultrasonic imaging systems comprising such MEMS switchable switch pMUT arrays.

BRIEF DESCRIPTION OF THE DRAWINGS

Embodiments of the present invention are illustrated by way of example, and not limitation, in the figures of the accompanying drawings in which:

FIG. 4A is a schematic view of a MEMS switchable 2D pMUT array, in accordance with an embodiment;

DETAILED DESCRIPTION

In the following description, numerous details are set forth. It will be apparent, however, to one skilled in the art, that the present invention may be practiced without these specific details. In some instances, well-known methods and devices are shown in block diagram form, rather than in detail, to avoid obscuring the present invention. Reference throughout this specification to "an embodiment" or "in one embodiment" means that a particular feature, structure, function, or characteristic described in connection with the embodiment is included in at least one embodiment of the invention. Thus, the appearances of the phrase "in an embodiment" in various places throughout this specification are not necessarily referring to the same embodiment of the invention. Furthermore, the particular features, structures, functions, or characteristics may be combined in any suitable manner in one or more embodiments. For example, a first embodiment may be combined with a second embodiment anywhere the two embodiments are not mutually exclusive.

The terms "coupled" and "connected," along with their derivatives, may be used herein to describe structural relationships between components. It should be understood that these terms are not intended as synonyms for each other. Rather, in particular embodiments, "connected" may be used to indicate that two or more elements are in direct physical or electrical contact with each other. "Coupled" my be used to indicated that two or more elements are in either direct or indirect (with other intervening elements between them) physical or electrical contact with each other, and/or that the two or more elements co-operate or interact with each other (e.g., as in a cause an effect relationship).

Figure 1A:
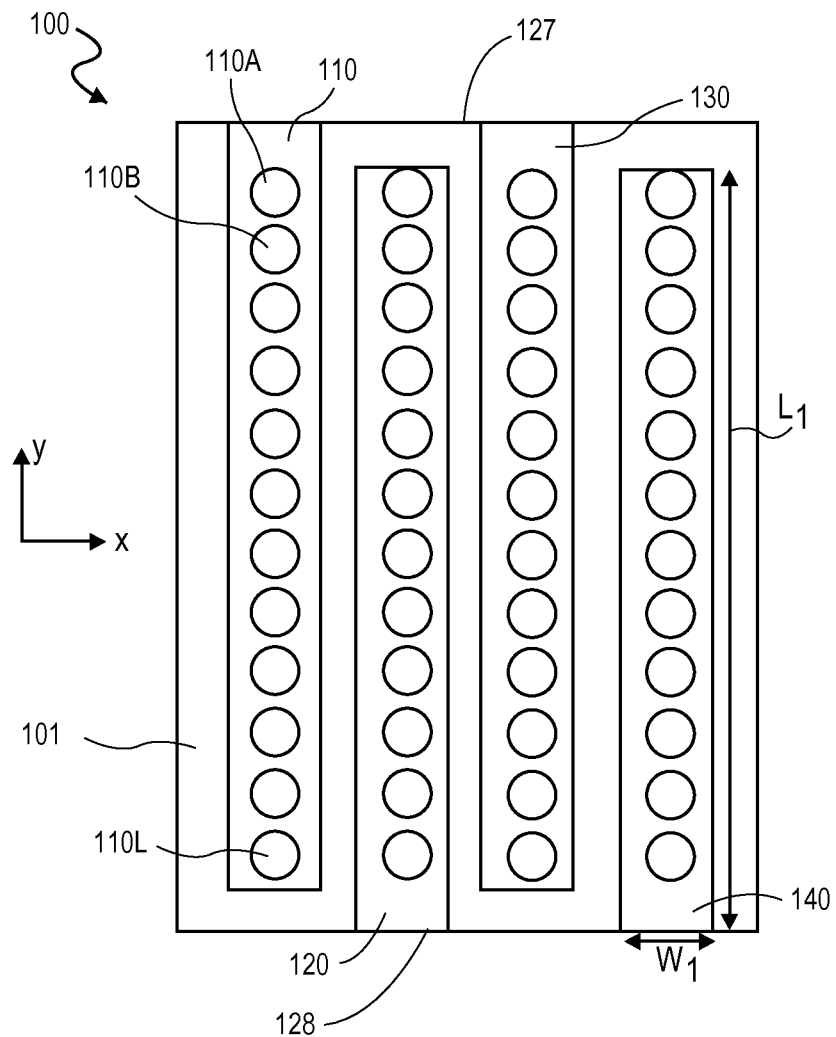
FIG. 1A is a plan view of a conventional 1D pMUT array with lumped transducer element access.
Figure 1B:
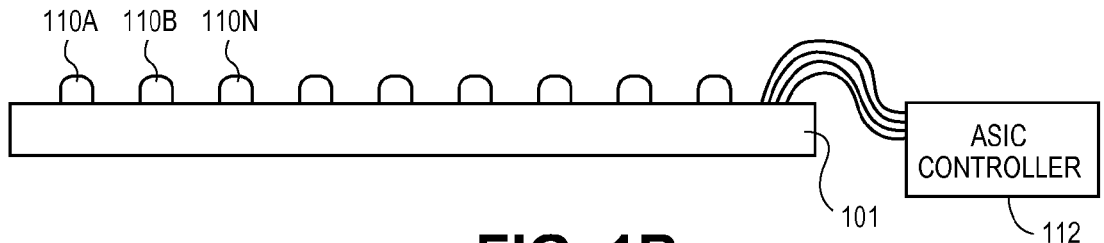
FIG. 1B is a cross-sectional side view of a substrate with the 1D pMUT array depicted in FIG. 1A, and coupled by a flex cable to a controller ASIC.
Figure 1C:
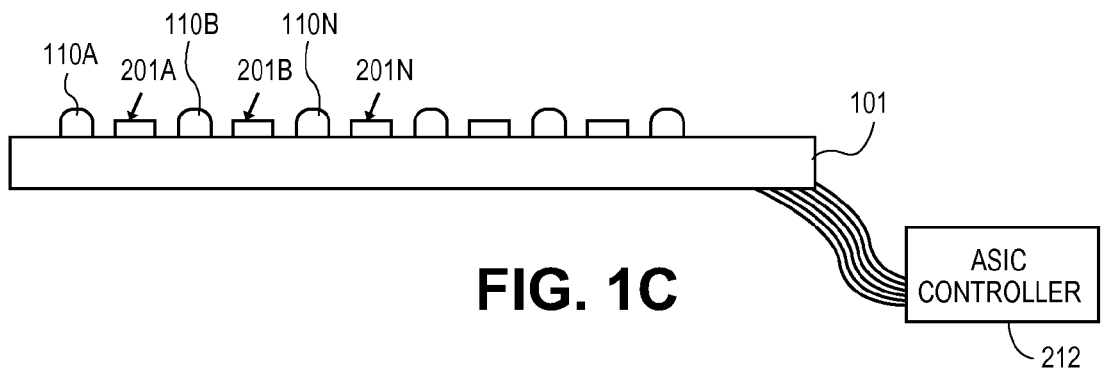
FIG. 1C is a cross-sectional side view of a substrate with a pMUT array integrated with MEMS switches on a same substrate, and coupled by a flex cable to a controller ASIC, in accordance with embodiments.

Switched micromachined transducer arrays including switchable transducer elements are described herein. In embodiments, a MEMS switch is integrated with transducer elements of an array. In one exemplary embodiment one or more MEMS switches are employed to provide fully addressable 2D transducer arrays. The MEMS switches may be further integrated to multiplex drive/sense channels coupled between the transducer array and drive/sense circuitry, thereby reducing interconnect routing demands for the transducer array and, where the array is fabricated on a substrate separate from that of the drive/sense circuitry, bandwidth of cable assemblies can be reduced relative to non-multiplexed implementations lacking switchable transducer elements. FIG. 1C is a cross-sectional side view of a substrate 101 with a pMUT array including transducer elements 110A, 110B, 110N integrated with MEMS switches 201A, 201B, 201N on the substrate 101, which is then coupled to a controller ASIC 212 by a flex cable, in accordance with embodiments. For such embodiments, the ASIC 212 is operable to both send and receive signals associated with the ultrasonic drive and sense modes of the transducer elements 110A, 110B, 110N and to further control switching of the MEMS switches 201A, 201B, 201N.

Figure 1D:
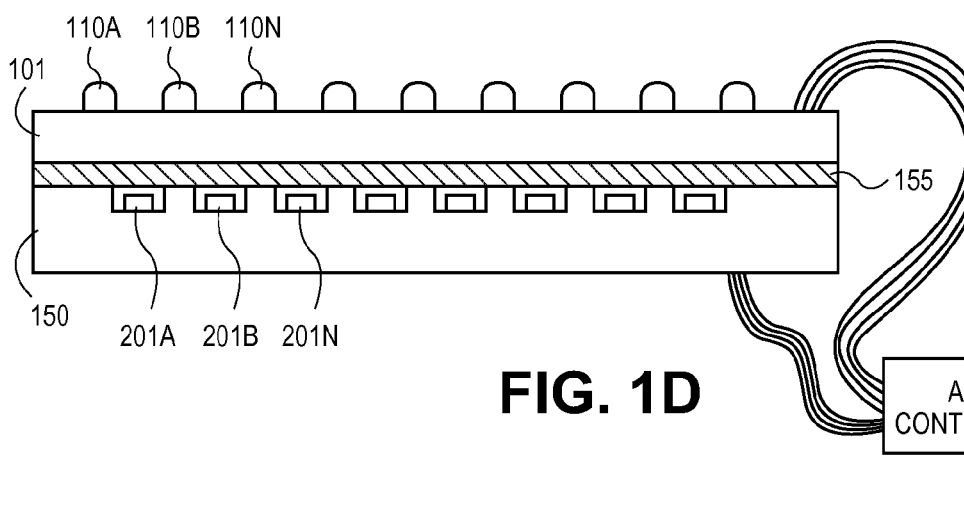
FIG. 1D is a cross-sectional side view of a first substrate with a pMUT array bonded to a second substrate with MEMS switches to form a 3D integrated device that is coupled by a flex cable to a controller ASIC, in accordance with embodiments.

In embodiments, MEMS switches are integrated with pMUT arrays through 3D integration techniques. For such embodiments, a substrate with MEMS switches is physically bonded or otherwise affixed to a substrate with pMUT arrays, either at a wafer-level or a chip-level. FIG. 1D is a cross-sectional side view of a first substrate 101 with a pMUT array including transducer elements 110A, 110B, 110N, bonded to a second substrate 150 having MEMS switches 201A, 201B, 201N, to form a 3D integrated device that is then coupled by a flex cable to the controller ASIC 212, in accordance with embodiments. For such embodiments, any bonding technique known in the art (e.g., a eutectic layer 155, etc.) may be utilized.

Figure 1E:
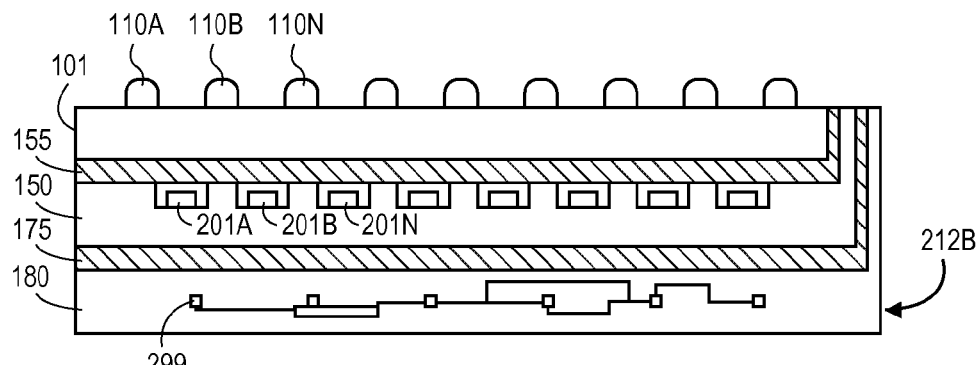
FIG. 1E is a cross-sectional side view of a first substrate with a pMUT array bonded to a second substrate with MEMS switches bonded to a CMOS substrate to form a fully integrated pMUT device.

In embodiments, MEMS switches are integrated with pMUT arrays and with CMOS logic through 3D integration techniques. For such embodiments, a substrate with MEMS switches is physically affixed to a substrate with pMUT arrays, which is further affixed to a substrate on which CMOS circuitry including transistors 299 is disposed. FIG. 1E is a cross-sectional side view of a first substrate 101 with a pMUT array including transducer elements 110A, 110B, 110N, bonded to a second substrate 150 having MEMS switches 201A, 201B, 201N, bonded to a third substrate 180 to form a 3D integrated device that is then packaged. For such highly integrated embodiments, the complexity of flex cable connections to the packaged device can be greatly reduced. Here too, any 3D stacking techniques known in the art (e.g., a eutectic layer 155, a build-up layer 175, etc.) may be utilized.

Generally, switched micromachined transducer arrays described herein may be premised on any known transducer technology, including, but not limited to, capacitive and piezoelectric principles. In the exemplary embodiments, the MEMS switch relies on the same transduction principles as that of the transducer arrays to effect a selection of one or more of the transducer elements in the array. For example, where the transducer array employs capacitive transducer elements, an integrated MEMS switch employs a capacitively controlled switching element, and for a piezoelectric transducer array, an integrated MEMS switch employs a piezoelectric switching element. Notably, even where a same transduction principle is shared between a MEMS switch and a transducer, the resonant frequency of the MEMS switch may be considerably different than that of a transducer element (e.g., significantly higher or lower). Also while a common transduction principle between the MEMS switch and the transducer is advantageous from the standpoint of most directly integrating a MEMS switch into a given transducer fabrication process, alternative embodiments where a MEMS switch and the transducer rely on different transduction principles (e.g., a capacitive MEMS switch integrated with a piezoelectric transducer, etc.) are also possible. Similarly, while detailed description is provided primarily in the context of piezoelectric transducer arrays, in part because of technical advantages over competing technologies (e.g., piezoelectric transducers currently achieve higher sensitivity than capacitive transducers), and in part for sake of clarity of description, one of skill in the art will appreciate the principles described herein may be readily applied to other known transducer technologies (e.g., capacitive, electromagnetic, etc.).

Figure 2A:
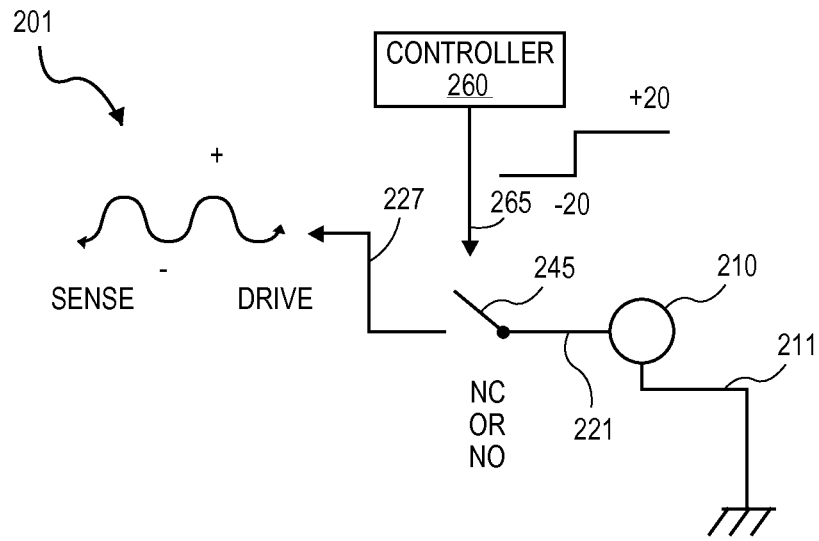
FIG. 2A is a schematic of a MEMS switchable pMUT, in accordance with an embodiment.

In embodiments, a micromachined transducer array includes at least one MEMS switchable piezoelectric micromachined transducer (pMUT) element. FIG. 2A is a schematic of a MEMS switchable PMUT 201, in accordance with an embodiment. A transducer element including a piezoelectric membrane 210 is coupled, via a reference electrode 211, to a reference potential, such as ground. While the piezoelectric membrane 210 may have a fundamental resonance anywhere within a wide frequency band, depending on design and application, in exemplary embodiments, the piezoelectric membrane 210 has resonance in the ultrasonic band (e.g., 100 kHz-100 MHz and more specifically 1 MHz-50 MHz) such that the pMUT 201 is a piezoelectric micromachined ultrasonic transducer (pMUT).

The piezoelectric membrane 210 is further coupled to a drive/sense electrode 221. In embodiments at least one of a reference electrode and the drive/sense electrode is coupled to a pole of a MEMS switch implemented over the same substrate as is the piezoelectric membrane 210 is disposed. In other words the MEMS switch 245 is monolithically integrated onto a transducer substrate. As shown in FIG. 2A for example, the drive/sense electrode 221 is coupled to a first pole of the MEMS switch 245 while a second pole of the MEMS switch 245 is coupled to a drive/sense channel 227. In such a configuration the MEMS switch 245 is operable to switchably pass a time varying sense or drive voltage signal between the drive/sense electrode 221 and the drive/sense channel 227. A MEMS switch may be configured in either a series or shunting configuration. In certain alternative embodiments for example, a MEMS switch may be disposed in between the reference electrode 211 and the reference potential to switchably float the reference electrode potential.

Generally, the MEMS switch 245 may comprise a switching member, or throw, that is either normally closed (NC) or normally opened (NO), as dependent at least on the electromechanics of the switching member. Depending on the embodiment, any of electrostatic, piezoelectric and electromagnetic techniques may be utilized to achieve a lateral or vertical deflection of the switching member in the MEMS switch 245. Also depending on the embodiment, the switching frequency of the MEMS switch 245 may vary widely as a function of the MEMS switch function. In one embodiment, the MEMS switch 245 is an RF or microwave MEMS switch having microsecond actuation times, or better. The MEMS switch 245 may be capacitive with a sufficiently small capacitance to capacitively couple all frequencies within the bandwidth of a transducer element. Capacitive switch embodiments have advantages over ohmic MEMS switch embodiments with respect to operational resilience, manufacturability, etc. Nevertheless, the MEMS switch 245 may also be implemented as an ohmic switch making metal-to-metal contact in the closed state. For either capacitive or ohmic switch embodiments, the MEMS switch 245 is to cause a conductive path between switched poles to undergo a change from a large impedance in an open switch state to low impedance (e.g., a short circuit) in a closed switch state. MEMS switches based on ohmic contact are advantageous for the transducer 'drive' mode, in which high voltage pulses with non-zero DC value are transmitted.

Figure 2B:
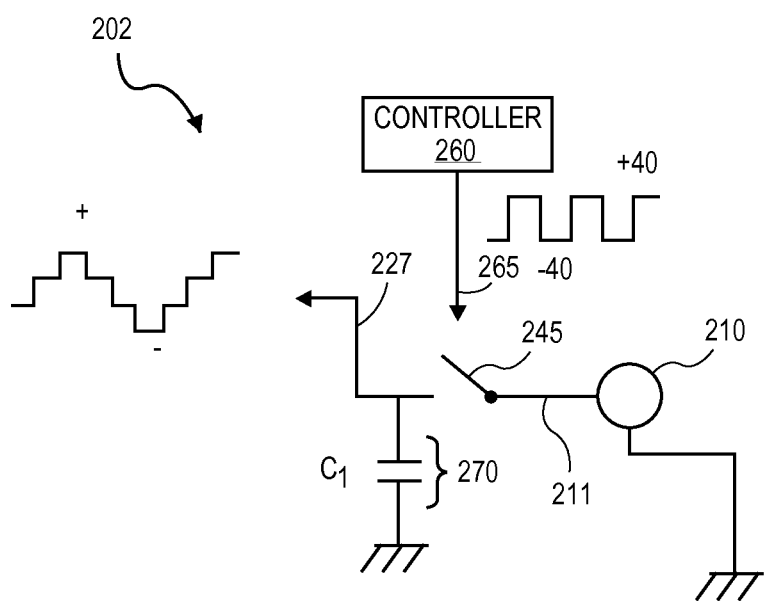
FIG. 2B is a schematic of a MEMS switchable pMUT including integrated sample and hold circuitry, in accordance with an embodiment.

As further illustrated in FIG. 2A, the MEMS switch 245 is coupled to a controller 260. The controller 260 provides a control signal 265, which for example entails a voltage step of sufficient magnitude (e.g., 1V-100 V) to change the state of the MEMS switch 245 as a function of time (e.g., at a lower switching frequency than frequencies passed by the switch as illustrated in FIG. 2A, or at higher switching frequency than frequencies passed as illustrated in FIG. 2B.). In first embodiments, the controller 260 further includes logic gates implemented with additional MEMS switches, for example further coupled to a controlled high voltage source. For such embodiments, the controller 260 may be monolithically integrated onto the transducer substrate, along with the MEMS switch 245. In second embodiments, the controller 260 is implemented off the transducer substrate, for example in a CMOS ASIC.

In further embodiments, a MEMS switch is integrated with a sample and hold (S/H) circuit. While many sample and hold circuits are known in the electrical arts, typical implementations include at least one switch and at least one capacitor. FIG. 2B is a schematic of a MEMS switchable pMUT 202 including integrated sample and hold circuitry, in accordance with an embodiment where the MEMS switch 245 forms a portion of the sample and hold circuitry. In the MEMS switchable pMUT 202, a capacitor 270 couples the drive/sense channel 227 to a reference (ground) potential and is to hold a reference potential sampled from the piezoelectric sense/drive electrode 211 after the MEMS switch 245 is set to an open state, disconnecting the sense/drive electrode 211 from the sense/drive channel 227. Depending on the implementation, the capacitor 270 may be a metal-insulator-metal (MIM) structure, for example, monolithically integrated on the transducer substrate, or a MOS capacitor, MIM, etc. integrated into an ASIC off the transducer substrate. Readout of the channel 227 may then be subsequently performed, for example with the assistance of one or more buffers or drivers, which may be implemented in a CMOS ASIC for example. A second MEMS switch (not depicted) connected between the capacitor 270 and the channel 227 may also be coupled to each transducer element. With sample and hold circuitry, the MEMS switch 245 may, if of sufficient switching speed, facilitate sampling of a time varying analog voltage waveform output by the transducer in addition to enabling switchable access to a single transducer element.

Figure 3A:
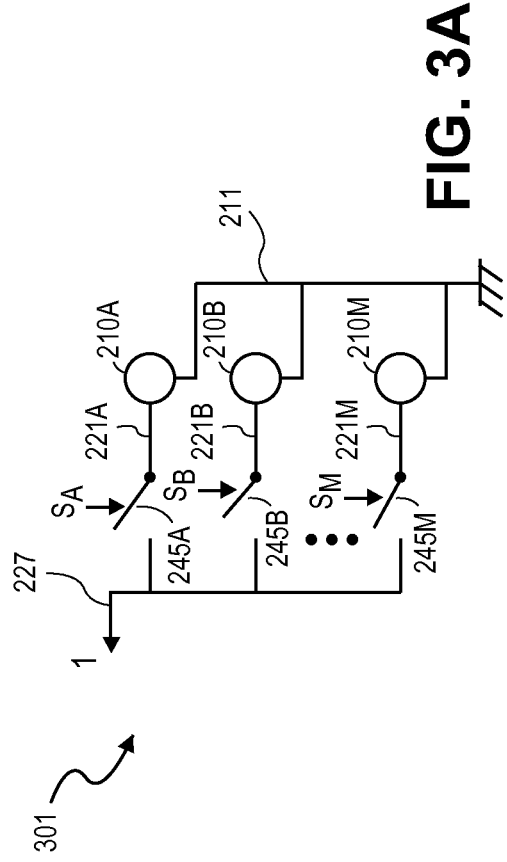
FIG. 3A is a schematic view of a MEMS switchable 1D pMUT array, in accordance with an embodiment.

In embodiments, a transducer array is integrated with a plurality of MEMS switches with states of the MEMS switches to control access to individual transducer elements. FIG. 3A is a schematic view of a MEMS switchable 1D pMUT array 301, in accordance with an embodiment. As shown, a plurality of piezoelectric membranes 210A, 210B, 210M forming a linear, columnar array have reference electrodes 211 all tied to a ground reference potential while each drive/sense electrode 221A, 221B, 221M is accessed via a separate MEMS switch 245A, 245B, 245M, respectively. With transducers coupled at an individual level to MEMS switches, each transducer of the linear array is independently accessible through switch control signals $S_A$, $S_B$, $S_M$. Depending on the implementation, the control signals $S_A$, $S_B$, $S_M$ may be generated with logic circuitry monolithically integrated on the transducer substrate (e.g., with additional MEMS switches) or with logic external circuitry provided off the transducer substrate (e.g., through a multiplexed control signal).

Figure 7A:
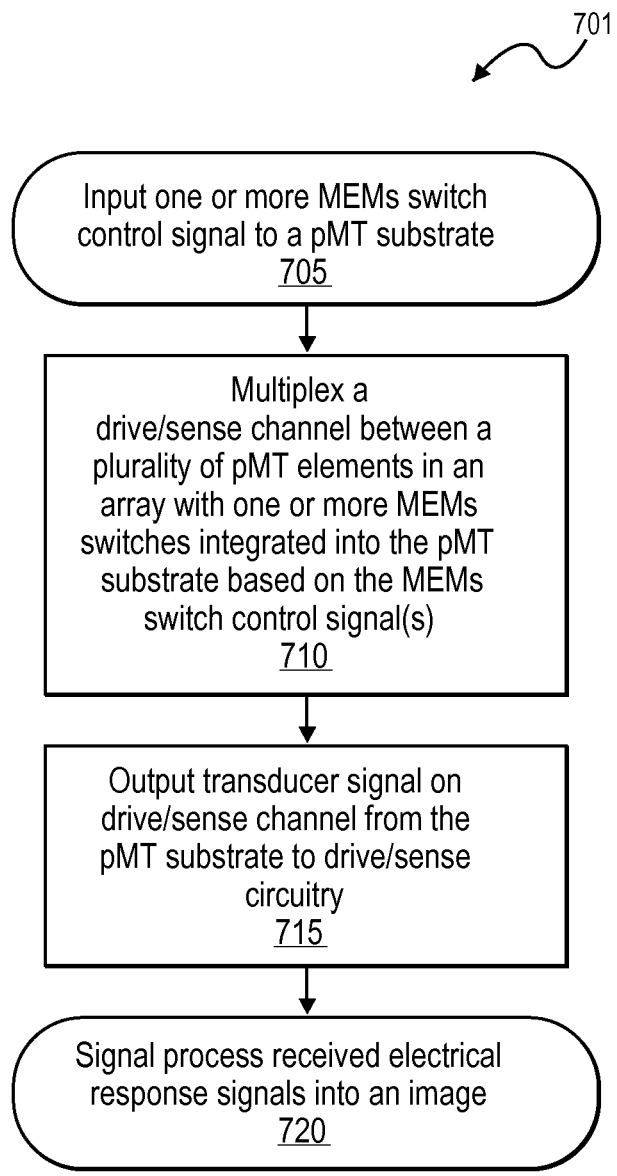
FIGS. 7A and 7B are a flow diagrams illustrating methods of independently addressing transducer elements of 2D array, in accordance with an embodiment.

Each transducer element may be selectably driven and sensed through the one drive/sense channel 227 at a different clock cycle or time (i.e., the drive sense channel 227 is multiplexed in MEMS switchable 1D pMUT array 301). FIG. 7A is a flow diagram illustrating a method 701 of independently addressing transducer elements of a transducer array, such as that illustrated in FIG. 3A, in accordance with an embodiment. The method 701 begins with inputting a MEMS switch control signal to a pMUT substrate at operation 705. The MEMS switch control signal may, for example, be originated by an ASIC off the pMUT substrate. At operation 710, a drive/sense channel is multiplexed between a plurality of pMUT elements in the array using one or more MEMS switches integrated into the pMUT substrate, for example as illustrated by FIG. 3A, based on a received MEMS switch control signal (e.g., $S_A$). At operation 715, a transducer response signal from a particular transducer is output on the drive/sense channel from the pMUT substrate to drive/sense circuitry implemented for example in CMOS logic in an ASIC off the pMUT substrate. Method 701 completes with operation 720 where the transducer response signal is processed, for example into an image in the example of pMUT imaging apparatus.

Figure 3B:
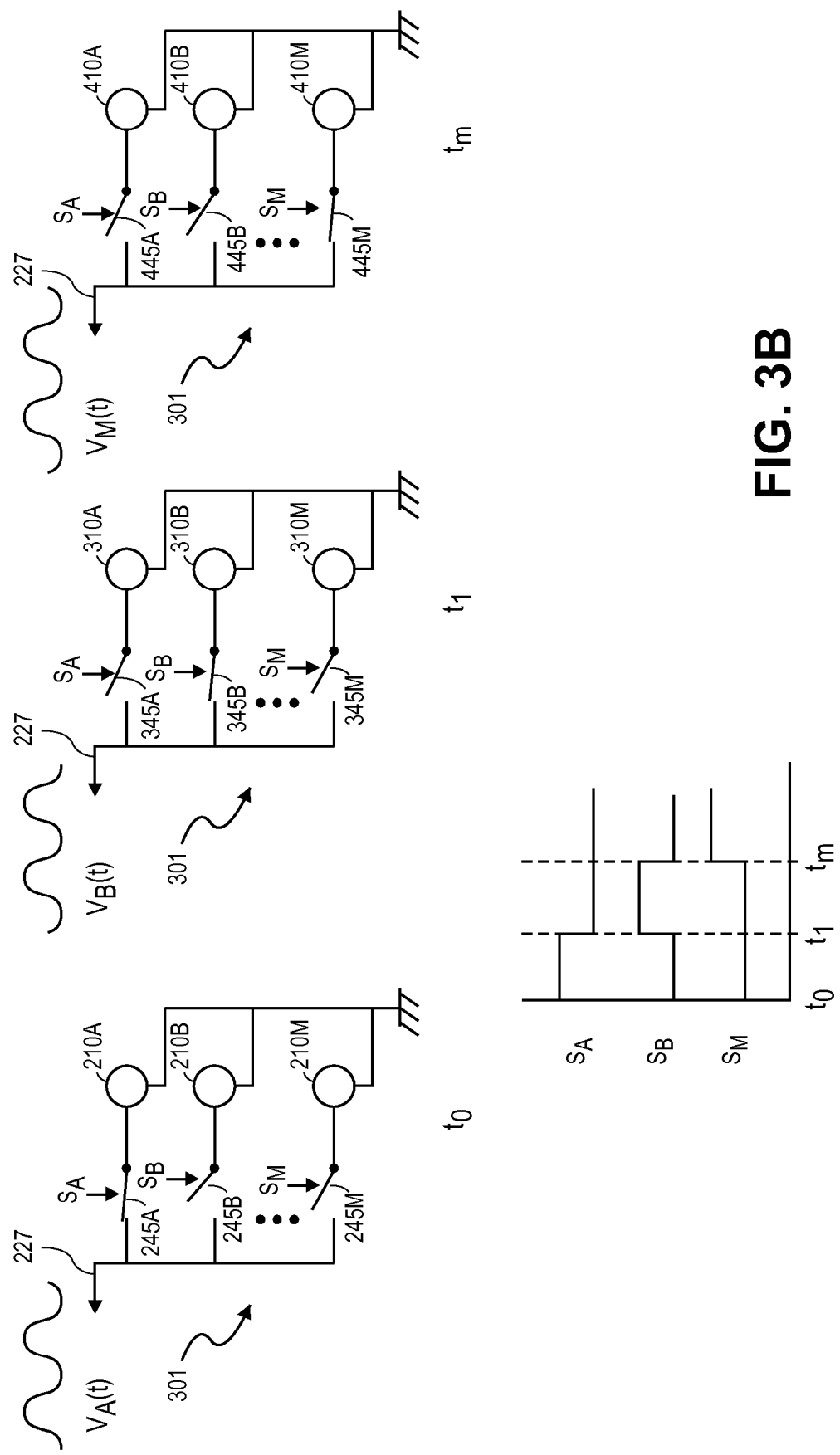
FIG. 3B is a schematic view of the MEMS switchable 1D pMUT array of FIG. 3A in different switched states over time according to the depicted timing diagram, in accordance with an embodiment.

FIG. 3B is a schematic view of the MEMS switchable 1D pMUT array 301 in different switched states over time as the method 701 is performed according to the depicted timing diagram, in accordance with an embodiment. Generally, the MEMS switchable 1D pMUT array 301 scans through the plurality of drive/sense electrodes 221 to couple an individual transducer to the drive/sense channel 227 for output off the transducer substrate. The control signals $S_A$, $S_B$, and $S_M$ are out of phase, each delayed after the former such that the MEMS switch array couples only one of transducer drive/sense electrode 221A, 221B, 221M to the drive/sense channel 227 at a time at least while the drive/sense channel 227 is in sense mode. As such, at a first time $t_0$, the MEMS switch 245A is in a low impedance, or closed, state, while the MEMS switches 245B and 245M are in high impedance, or open states, and a time varying waveform $V_A(t)$ is passed to/from the drive/sense channel 227. At a second time $t_1$, the MEMS switch 245B is in a low impedance state, while the MEMS switches 245A and 245M are in high impedance states, and the time varying waveform $V_B(t)$ is passed to/from the drive/sense channel 227. At an $m^{th}$ time $t_m$, the MEMS switch 245M is in a low impedance state, while the MEMS switches 245A and 245B are in high impedance states and the time varying waveform $V_M(t)$ is passed to/from the drive/sense channel 227.

Figure 4B:
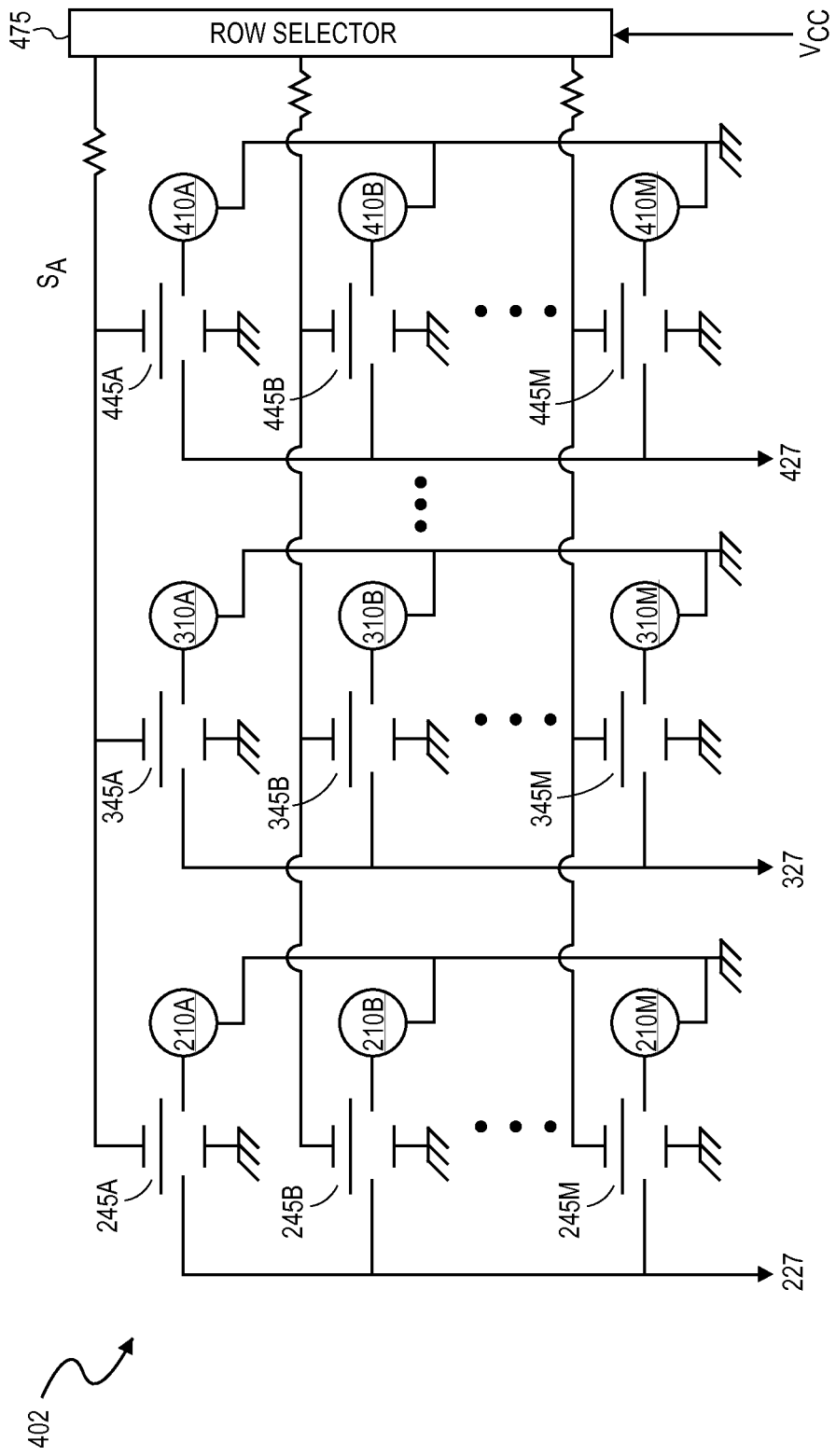
FIG. 4B is a schematic view of a MEMS switchable 2D pMUT array, in accordance with an embodiment.

In further embodiments, MEMS switchable micromachined transducer array provides independent transducer element addressing within a 2D array of transducer elements. FIG. 4B is a schematic view of a MEMS switchable 2D pMUT array 401, in accordance with one exemplary embodiment. Generally the 2D pMUT array 401 includes a plurality of the 1D linear pMUT arrays 301 arranged into separate columnar arrays with individual transducer elements of the adjacent columns being aligned into transducer element rows. Each transducer of the columnar arrays is selectably coupled by a MEMS switch to a signal drive/sense channel 227, 327, 427 with the 2D pMUT array 401 therefore having 1, 2, N drive/sense channels. In one exemplary embodiment, a plurality of MEMS switches are communicatively coupled to a same control signal (e.g., $S_A$, $S_B$, $S_M$) such that states of MEMS switches controlling access to one transducer element in each row are matched for one row of transducers to be selectively coupled to their respective drive/sense channels concurrently. For example, at a first time $t_0$, MEMS switches 245A, 345A, and 445A are controlled by a switch signal $S_A$ to a low impedance switch state coupling the piezoelectric membranes 210A, 310A, and 410A to the drive/sense channels 227A, 327A, 427A, respectively. In further embodiments, at $t_0$, MEMS switches 245B, 345B, 445B and 245M, 345M, 445M are controlled to high impedance states, decoupling all other transducer elements from the respective drive/sense channels.

Figure 7B:
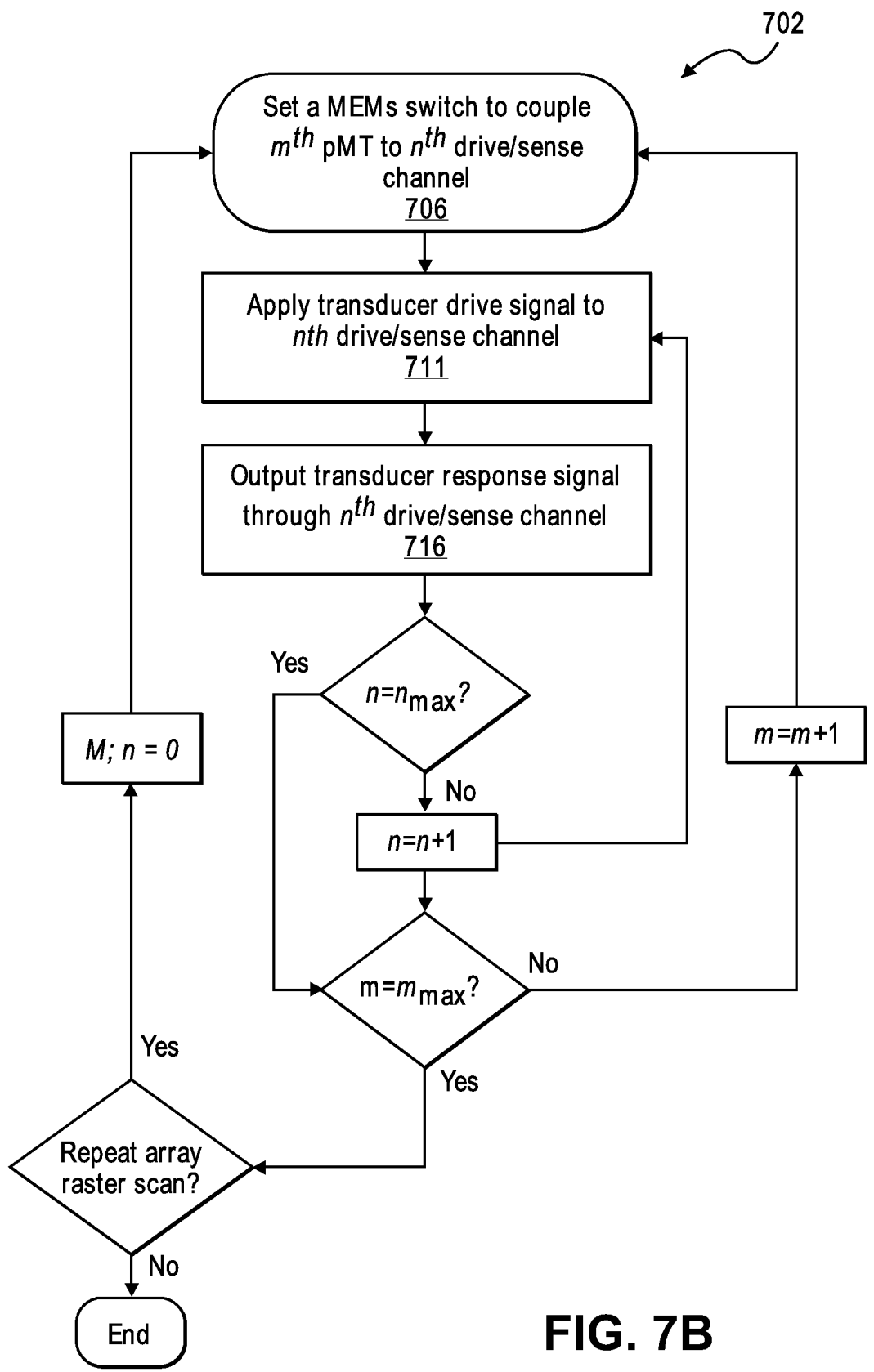

FIG. 7B is a flow diagram illustrating a method 702 for independently addressing transducer elements of a 2D transducer array, such as that illustrated in FIG. 3A, in accordance with an embodiment. The method 702 begins at operation 706 with setting a MEMS switch to couple a pMUT element to an associated drive/sense channel. At operation 711, a drive signal is applied to the associated drive/sense channel and at operation 716 a transducer response signal is received. Any conventional means may be utilized to drive and sense a signal to/from the drive/sense channel. For all other drive/sense channels, the method 702 repeats operations 711 and 712 to sample responses from other pMUT elements in the array rendered accessible by the switch states set at operation 706. Depending on the embodiment, n channels may be driven and responses read out either simultaneously or in a phased, time delayed manner. Upon reading out all channels for a given MEMS switch state, method 702 advances into a different MEMS switch state that places an alternate transducer element in communication with the associated drive/sense channel. With the new MEMS switch state set at operation 706, operations 711 and 712 are then repeated. The method 702 proceeds in this manner until the entire array has been read out, at which point the signal processing of the read data may be performed with logic off the pMUT substrate, for example processed into a 3D image where the 2D array is a pMUT of an ultrasonic imaging apparatus. The method 702 is repeated indefinitely as a means of refreshing the raster scan and associated 3D image.

As so described, the MEMS switchable 2D pMUT array 401 (FIG. 4A) is amenable to multiplexing of the switch control signals across separate subsets of transducer elements to scan through individual transducers along a first dimension of the array. In further embodiments, the separate drive/sense channels 227, 327, and 427 may all be driven and/or sensed out of phase (e.g., with a known time delay between channels corresponding to physically adjacent linear arrays of transducer elements) for individual transducer-level 1D phased array operation. For such an embodiment, a 2D arrayed population of elements is raster scanned. In other embodiments, the separate drive/sense channels 227, 327, and 427 may all be driven in phase (e.g., with no time delay between channels) for 1D lump transducer operation. In still other embodiments, where control signals $S_A$, $S_B$, $S_M$ place all MEMS switches in low impedance states concurrently, conventional 1D lumped array operation is achieved with the further ability to switch the orientation of the 1D array orthogonally dynamically during operation as a function of the MEMS switch states.

With multiplexing of the MEMS switch control signals, only 2n channels to/from the transducer substrate may be needed to individually access/address transducer elements within a square n channel array. FIG. 4B is another schematic view of a MEMS switchable 2D pMUT array 402. Generally, the array 402 further illustrates common coupling of control signals across a plurality of MEMS switches as an exemplary transducer multiplexing architecture. In FIG. 4B, reference numbers shared in common with FIG. 4A represent the same features described in FIG. 4A. As further shown in FIG. 4B, where the MEMS switches are of suitable performance, a row selector 475 may be implemented monolithically on the transducer substrate. Generally, the row selector 475 is a demultiplexer and many CMOS logic circuits are known in the art for implementing such a circuit. In certain embodiments where one or more MEMS switches implement logic gates of a row selector, only n channels to/from the transducer substrate may be needed to individually access/address transducer elements within a square n channel array. In further embodiments, where MEMS switches further implement selection of channels, a multiplexing of the channels 227, 327, 427 becomes possible with a concomitantly large reduction in the cable assembly needed between ASIC components and a transducer element of a given apparatus (e.g., print head, ultrasonic imager, etc.).

In other embodiments, a combination of MEMS switches can be configured and controlled to enable sampling of a sense signal output by one or more transducer elements or plurality of elements corresponding to a data channel. For example, two or more of the channels 227, 327, 427 may be selected (i.e., MEMS switch in closed state) concurrently during one or more drive/sense cycle. Similarly, two or more transducer elements from one or more of the channels 227, 327, 427 may be active (i.e., MEMS switch in closed state) concurrently during one or more drive/sense cycle.

In embodiments MEMS switches couple transducer elements to a capacitive storage array or bank. With the write and read of capacitor elements controlled by MEMS switches, sampled sense output signals may be stored upstream of an ASIC and subsequently read out. As such, the switched capacitive storage bank may be employed for signal transfer, to add or integrate across multiple transducer elements or groups (i.e., channels) of elements, etc. The MEMS switches may be integrated on the same substrate as the transducers and the capacitive elements may be integrated on a same substrate as the MEMS switches or on a separate substrate.

Figure 4C:
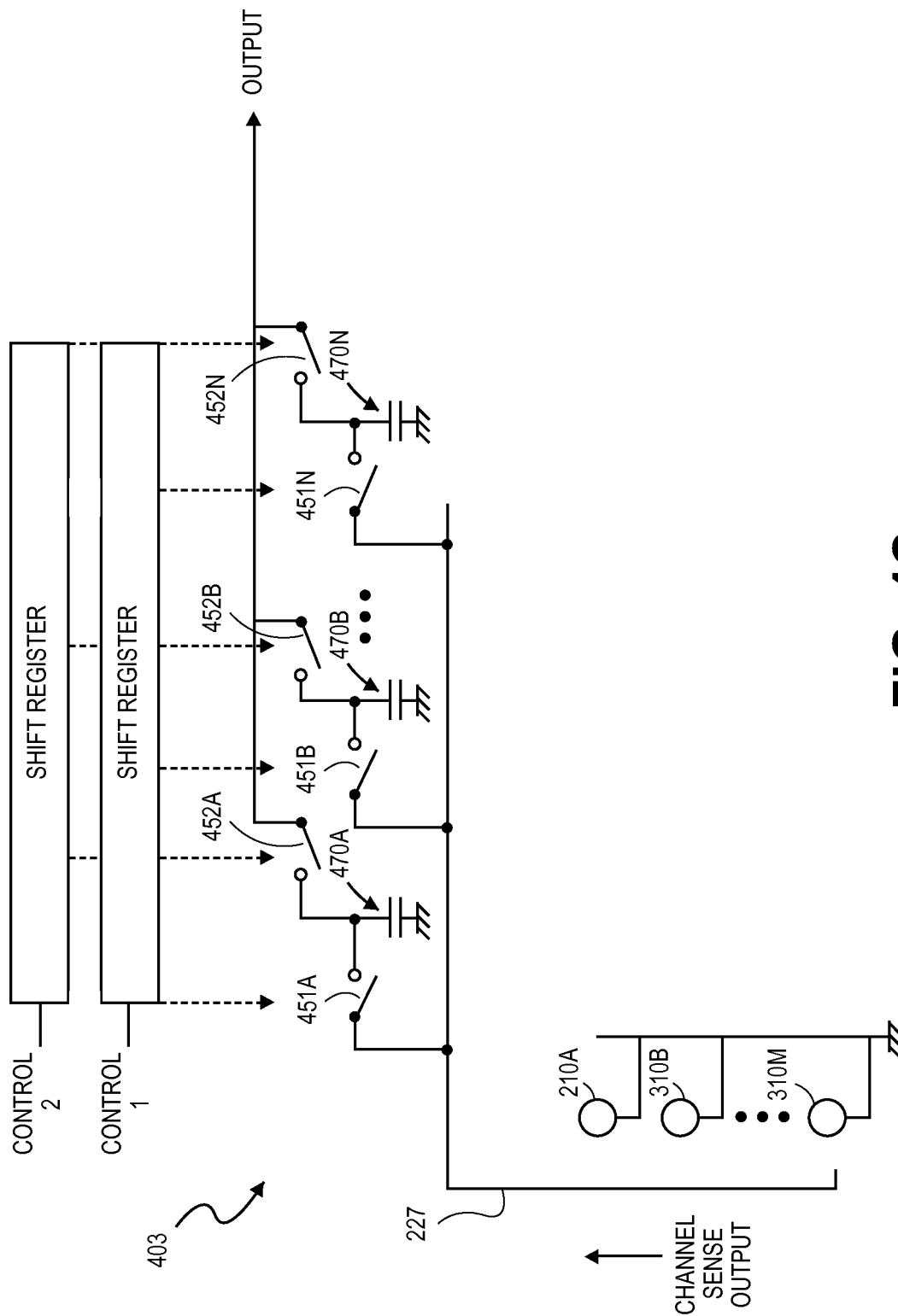
FIG. 4C is a schematic of a MEMS switchable pMUT including integrated sample and hold circuitry, in accordance with an embodiment.

FIG. 4C illustrates an exemplary system 403 where a voltage output from transducer element channels are transferred to capacitive storage elements. In the schematic view depicted in FIG. 4, the transducer channel 227 is coupled to the transducer elements 210A-310M. Coupling between the channel bus and individual transducer elements may also be via a MEMS switch, for example as described in the context of FIGS. 2-3. The channel 227 is further coupled to a switched capacitor bank including capacitive elements 470A, 470B, and 470N. MEMS switches 451A, 451B and 451N having bi-stable states controlled by a first control signal selectively couple the channel 227 to the capacitive elements 470A-470N. The switches 451A-451N may be open during the drive mode of the channel 227 and successively closed as the channel 227 outputs a time varying voltage signal while in the sense mode. In one embodiment, for example, the first control signal clocks a shift register (e.g., implemented on a downstream ASIC) to successively sample the sense single from channel 227 into a capacitor on successive clock signals. When each switch 451A-451N closes, the instantaneous value of the sense signal 227 is stored to a corresponding capacitor 470A-470N.

With the sense signal samples from the channel 227 stored, switches 451A-451N are all opened and contents of the capacitor bank available for read out, for example to a downstream ASIC. As further depicted in FIG. 4C, MEMS switches 452A, 452B and 452N having bi-stable states controlled by a second control signal may be utilized for successively reading out the capacitive elements, for example as sequenced by a second shift register at a later time. A continuous time varying signal can be generated, for example by coupling the sequenced output of the capacitor bank to a conventional integrator. Alternatively, the sampled sense signal may be delayed and subsequently summed, or otherwise operated upon along with similarly stored sense signals from other transducer channels. The delay interval would be set by the digital clock controls (Control 1 and Control 2) which can enable analog beamforming at the transducer side.

Figure 5A:
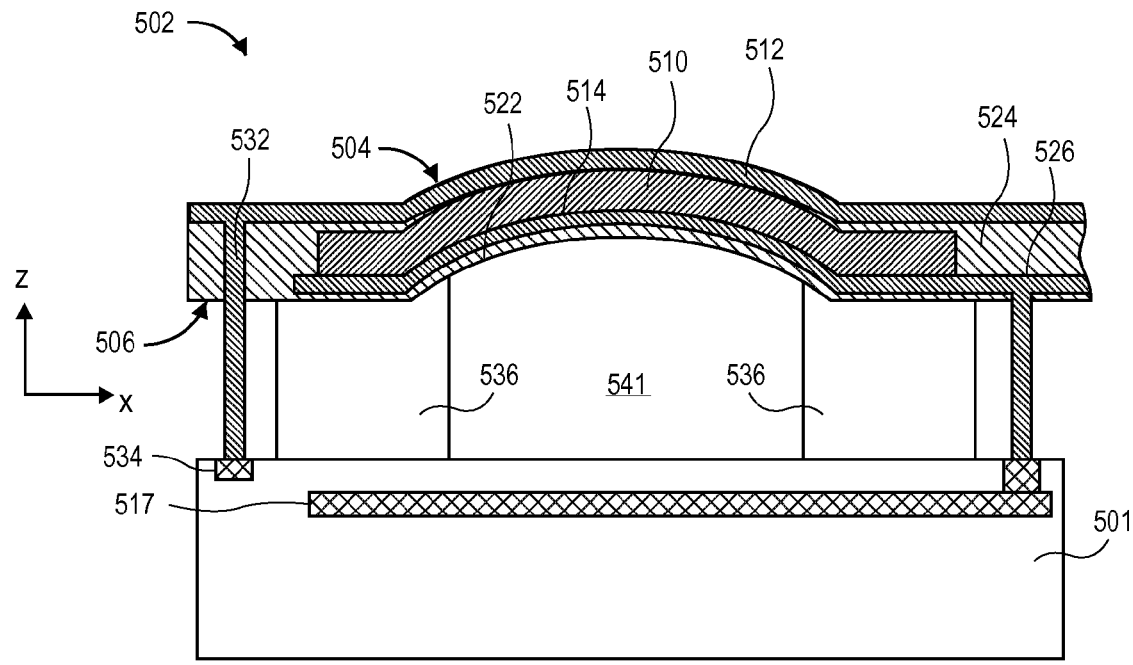
FIGS. 5A, 5B, and 5C are cross-sectional views of piezoelectric transducer elements, one or more of which is employed in a MEMS switchable pMUT array, in accordance with embodiments.
Figure 5B:
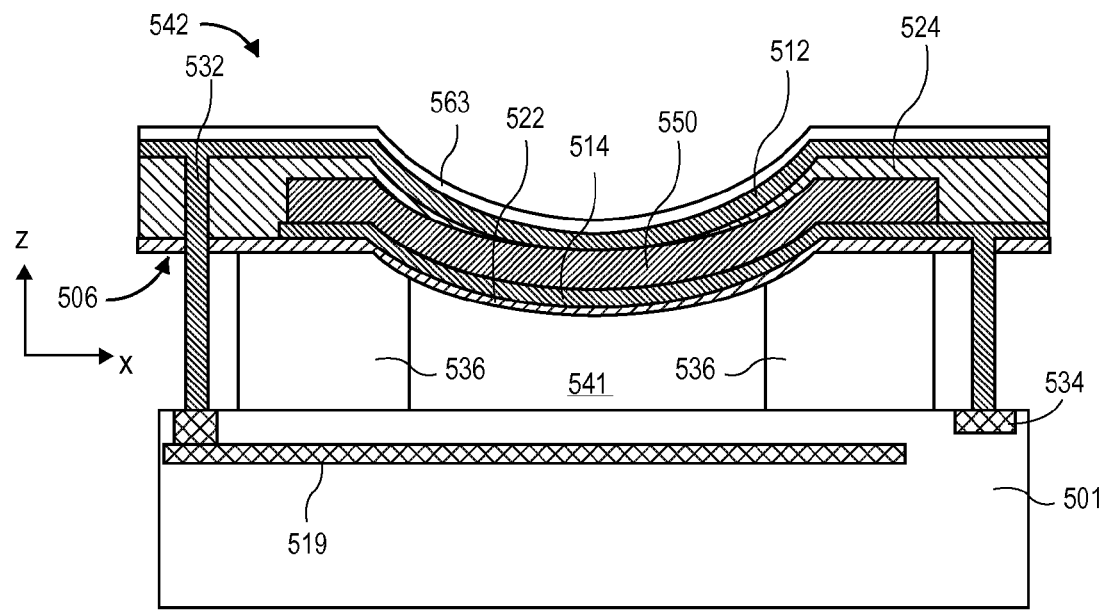
Figure 5C:
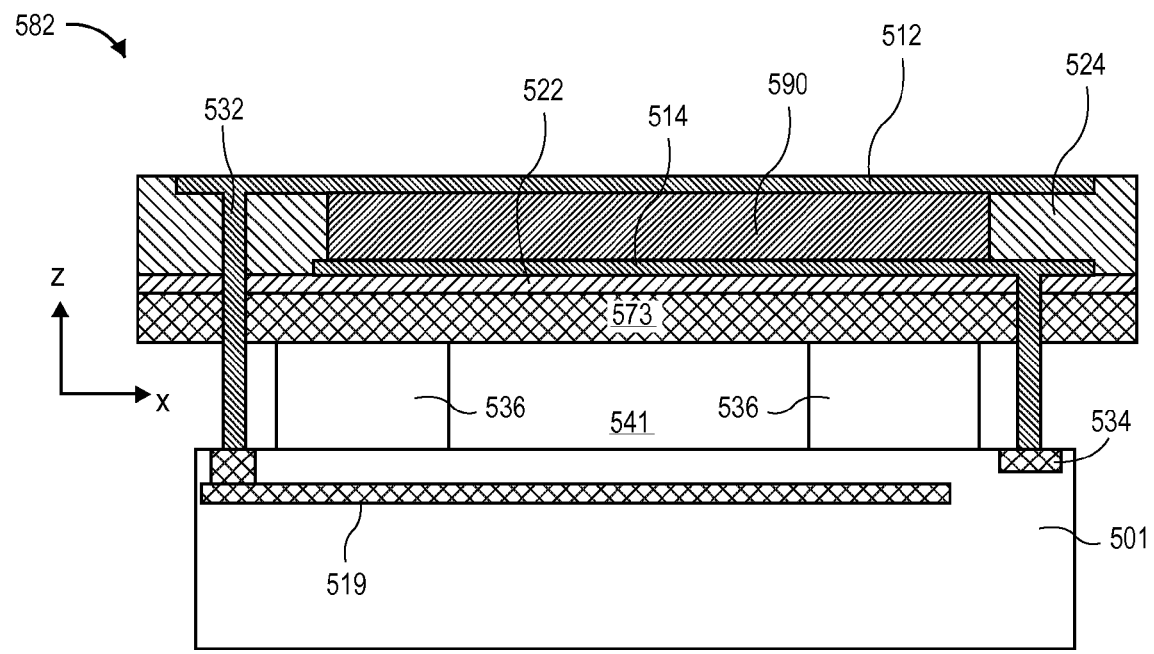
Figure 6:
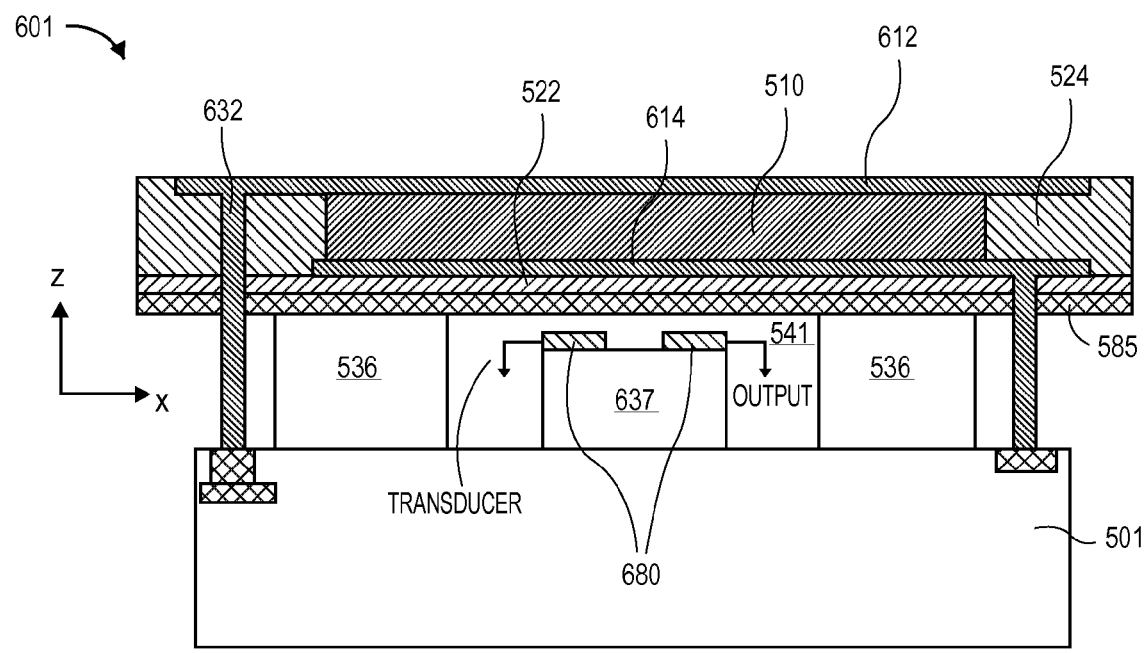
FIG. 6 is a cross-sectional view of a piezoelectric MEMS switch element which is employed in a MEMS switchable pMUT array, in accordance with an embodiment.

FIGS. 5A, 5B, and 5C are cross-sectional views of piezoelectric transducer elements, one or more of which may be employed in embodiments of a MEMS switchable pMUT array. In the context of FIGS. 5A-5C, exemplary structural aspects of individual transducer elements are now briefly described. It is to be appreciated that the structures depicted in FIGS. 5A-5C are included primarily as context for particular aspects of the present invention and to further illustrate the broad applicability of the present invention with respect to piezoelectric transducer element structure. FIG. 6 is a cross-sectional view of a piezoelectric switch element which may be employed in a MEMS switchable pMUT array, in accordance with an embodiment and further illustrates monolithic integration of a MEMS switch into a transducer substrate.

In FIG. 5A, a convex transducer element 502 includes a top surface 504 that during operation forms a portion of a vibrating outer surface of a MEMS switch pMUT array, for example. The transducer element 502 also includes a bottom surface 506 that is attached to a top surface of the transducer substrate 501. The transducer element 502 includes a convex or dome-shaped piezoelectric membrane 510 disposed between a reference electrode 512 and a drive/sense electrode 514. In one embodiment, the piezoelectric membrane 510 can be formed by depositing (e.g., sputtering) piezoelectric material particles in a uniform layer on a profile-transferring substrate (e.g., silicon) that has a dome formed on a planar top surface, for example. An exemplary piezoelectric material is Lead Zirconate Titanate (PZT), although any known in the art to be amenable to conventional micromachine processing may also be utilized, such as, but not limited to doped polymethylmethacrylate (PMM) polymer particles, Polyvinylidene fluoride (PVDF), single crystal PMN-PT, $BaTiO_3$ and aluminum nitride (AlN). The drive/sense electrode and reference electrode 514, 512 can each be a thin film layer of conductive material deposited (e.g., by PVD, ALD, CVD, etc.) on the profile-transferring substrate. The conductive materials for the drive electrode layer can be any known in the art for such function, such as, but not limited to, one or more of Au, Pt, Ni, Ir, etc.), alloys thereof (e.g., AdSn, IrTiW, AdTiW, AuNi, etc.), oxides thereof (e.g., $IrO_2$, $NiO_2$, $PtO_2$, etc.), or composite stacks of two or more such materials.

As further shown in FIG. 5A, in some implementations, the transducer element 502 can optionally include a thin film layer 522, such as silicon dioxide that can serve as a support and/or etch stop during fabrication. A dielectric membrane 524 may further serve to insulate the drive/sense electrode 514 from the reference electrode 512 in regions external to the piezoelectric membrane 510. Vertically-oriented electrical interconnect 526 connects the drive/sense electrode 514 to a drive/sense channel and/or a MEMS switch via the drive/sense electrode rail 517. A similar interconnect 532 connects the reference electrode 512 to a reference rail 534. An annular support 536, having a hole 541 with an axis of symmetry defining a center of the transducer element 502, mechanically couples the piezoelectric membrane 510 to the transducer substrate 501. The support 536 may be of any conventional material, such as, but not limited to, silicon dioxide, polycrystalline silicon, polycrystalline germanium, SiGe, and the like. Exemplary thicknesses of support 536 range from 10-100 μm and exemplary thickness of the membrane 524 range from 1-15 μm with exemplary diameters of the membrane 510 ranging from 10-200 μm for embodiments with fundamental resonance in the ultrasonic band, for example 1-50 MHz.

FIG. 5B shows another example configuration for a transducer element 542 in which structures functionally similar to those in transducer element 502 are identified with like reference numbers. The transducer element 542 illustrates a concave piezoelectric membrane 550 that is concave in a resting state. The drive/sense electrode 214 is disposed below the bottom surface of the concave piezoelectric membrane 550, while the reference electrode 512 is disposed above the top surface and coupled to the reference electrode rail 517.

FIG. 5C shows another example configuration for a transducer element 582 in which structures functionally similar to those in transducer element 502 are identified with like reference numbers. The transducer element 582 illustrates a planar piezoelectric membrane 590 that is planar in a resting state and unlike the elements 502, operates in bending mode and therefore further employs a membrane 575 (typically of silicon). Here again, the drive/sense electrode 514 is disposed below the bottom surface of the planar piezoelectric membrane 590, while the reference electrode 512 is disposed above the top surface. An opposite electrode configuration from that depicted in each of FIGS. 2A-2C is of course also possible.

FIG. 6 is a cross-sectional view of a piezoelectric MEMS switch element 601 which is employed in a MEMS switchable pMUT array, in accordance with an embodiment. To emphasize the monolithic nature of the MEMS switch element 601 and the transducer elements 502, 524 and 526, structures in FIG. 6 compatible with those in transducer elements of FIGS. 5A-5C are identified with like reference numbers. As illustrated, the MEMS switch element 601 includes a fixed beam switching member although in alternative embodiments a cantilever beam, etc. may be employed. The switch element includes the planar piezoelectric membrane 590 disposed over a membrane 585 (e.g., of metal or heavily doped silicon) suitable for bending mode operation. The switch drive electrode 614 is disposed below the bottom surface of the planar piezoelectric membrane 590, while a reference electrode 612 is disposed above the top surface of piezoelectric membrane 590. The order of electrodes can be reversed as well (i.e., top electrode can be used as the drive and the bottom electrode as the reference). The thin film layer 522, such as silicon dioxide dielectric layer, etc., serves a further function of blocking the drive signal from shorting to the lower electrodes 680 disposed on a recessed support 637 during switch actuation. When the piezoelectric membrane 590 deflects in response to a drive (control) signal, high frequency transducer signals may pass between the transducer and output electrodes 680. When no drive signal is present, and the piezoelectric membrane 590 is not deflected sufficiently, capacitive coupling is insufficient to pass the high frequency transducer drive/sense signals thereby selectably isolating or coupling a given transducer element. As many alternative switch architectures are known in the art, the interested reader is referred to the literature for further description of piezoelectric MEMS switches suitable for selectably accessing an individual pMUT element of an array.

Figure 8:
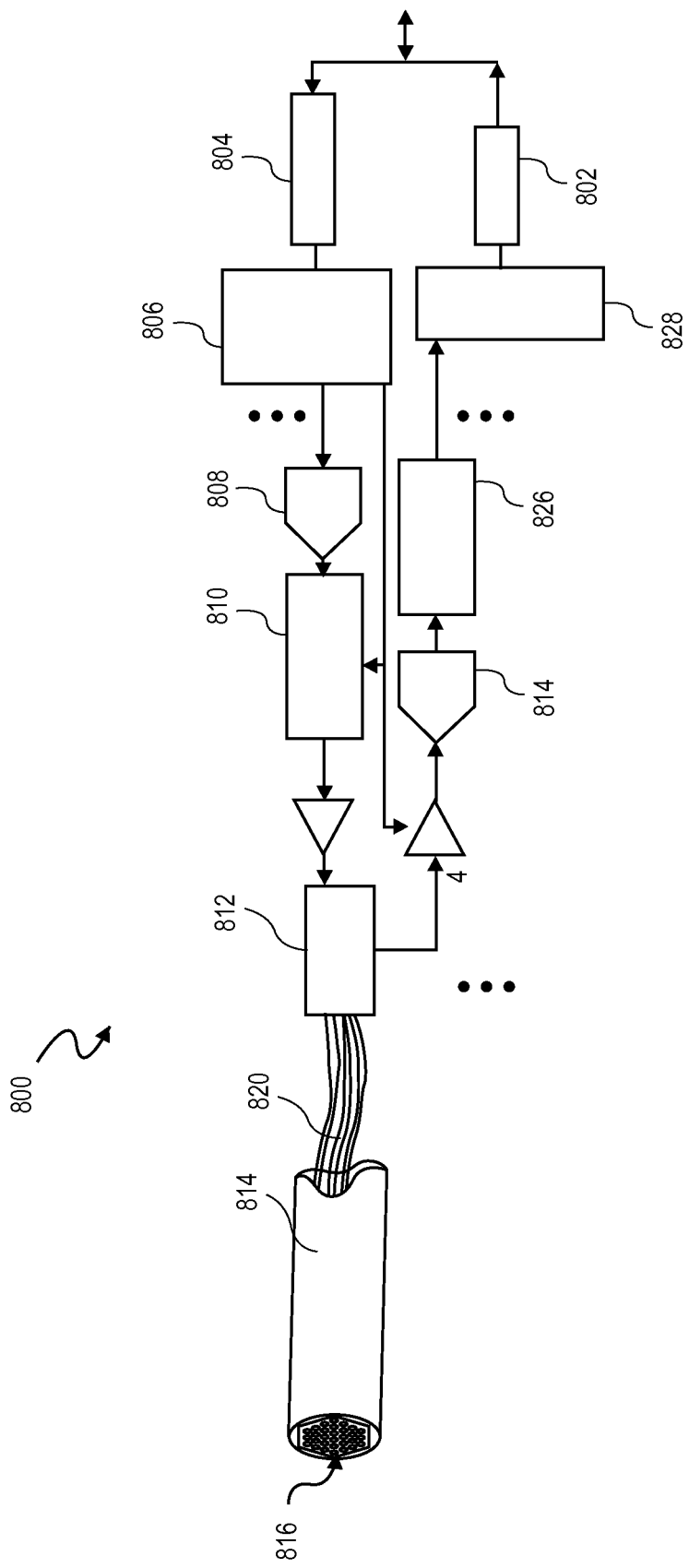
FIG. 8 is a functional block diagram of a print head which employs a micromachined piezoelectric array, in accordance with an embodiment of the present invention.

FIG. 8 is a functional block diagram of an ultrasonic transducer apparatus 800 that employs a pMUT array, in accordance with an embodiment of the present invention. In an exemplary embodiment, the ultrasonic transducer apparatus 800 is for generating and sensing pressure waves in a medium, such as water, tissue matter, etc. The ultrasonic transducer apparatus 800 has many applications in which imaging of internal structural variations within a medium or multiple media is of interest, such as in medical diagnostics, product defect detection, etc. The apparatus 800 includes at least one MEMS switchable pMUT array 816, which may be any of the MEMS switchable pMUT arrays described elsewhere herein having any of the MEMS addressable transducer elements. In exemplary embodiment, the MEMS switchable pMUT array 816 is a 2D transducer array housed in a handle portion 814 which may be manipulated by machine or by a user of the apparatus 800 to change the facing direction and location of the outer surface of the MEMS switchable pMUT array 816 as desired (e.g., facing the area(s) to be imaged). Electrical connector 820 electrically couples the drive/sense channels of the pMUT array 816 to a communication interface of the transducer substrate and external to the handle portion 814.

In embodiments, the apparatus 800 includes a signal generator, which may be any known in the art, coupled to the MEMS switchable pMUT array 816, for example by way of electrical connector 820. The signal generator is to provide an electrical drive signal on various drive/sense channels. In one specific embodiment, the signal generator is to apply an electrical drive signal to cause an addressed piezoelectric transducer element to resonate at frequencies between 1 MHz and 50 MHz. In certain embodiments, the signal generator is any high voltage pulse generator known in the art. In other embodiments where transmit beamforming is utilized, the signal generator includes a de-serializer 804 to de-serialize control signals that are then de-multiplexed by demux 806. A digital-to-analog converter (DAC) 808 is then to convert the digital control signals into driving voltage signals for the individual transducer element channels in the MEMS switchable pMUT array 816. Respective time delays can be added to the individual drive voltage signal by a programmable time-delay controller 810 to beam steer, create the desired beam shape, focus, and direction, etc. across channels of the array and/or across transducer elements of a given channel. Coupled between the pMUT channel connector 802 and the signal generator is a controller 812 responsible for sending MEMS switch control signals over control channels of the connector 802 to the MEMS switches of the MEMS switchable pMUT array 814. The controller 812 may further include a switch network to switch addressed transducer elements between drive and sense modes.

In embodiments, the apparatus 800 includes a signal receiver, which may be any known in the art, coupled to the MEMS switchable pMUT array 816, for example by way of electrical connector 820. The signal collecting means is to collect an electrical sense signal from the drive/sense electrode channels in the MEMS switchable pMUT array 816. In one exemplary embodiment of a signal collecting means, an analog to digital converter (ADC) 814 is to receive voltage signals and convert them to digital signals. The digital signals may then be stored to a memory (not depicted) or first passed to a signal processor. An exemplary signal processor includes a data compression unit 826 to compress the digital signals. A multiplexer 818 and a serializer 828 may further process the received signals before relaying them to a memory, other storage, or a downstream processor, such as an image processor that is to generate a graphical display based on the received signals.

It is to be understood that the above description is intended to be illustrative, and not restrictive. For example, while flow diagrams in the figures show a particular order of operations performed by certain embodiments of the invention, it should be understood that such order is not required (e.g., alternative embodiments may perform the operations in a different order, combine certain operations, overlap certain operations, etc.), unless an input of one operation inherently relies on an output of another operation. Furthermore, many other embodiments will be apparent to those of skill in the art upon reading and understanding the above description. For example, although an ultrasonic imaging apparatus is explicitly described, sufficient detail is provided for one of ordinary skill to apply a MEMS switchable piezoelectric array to other apparatuses, such as, but not limited to piezoelectric print heads. Therefore, although the present invention has been described with reference to specific exemplary embodiments, it will be recognized that the invention is not limited to the embodiments described, but can be practiced with modification and alteration within the scope of the appended claims. The scope of the invention should, therefore, be determined with reference to the appended claims, along with the full scope of equivalents to which such claims are entitled.

What is claimed is:

1. A piezoelectric micromachined transducer (pMUT) array, comprising:
a transducer substrate;
a plurality of piezoelectric transducers disposed over a first area of the transducer substrate; and
a plurality of MEMS switches coupled to the plurality of transducers, wherein states of the MEMS switches control access to individual transducers of the plurality.

2. The pMUT array of claim 1, wherein the MEMS switch comprises a piezoelectric, electrostatic or electromagnetic switching member and wherein the MEMS switches are disposed over a second area of the transducer substrate.

3. The pMUT array of claim 2, wherein the array is a two dimensional (2D) array, wherein the plurality of transducer elements are resonant within the ultrasonic frequency band, and wherein the MEMS switch comprises a piezoelectric member employing a same piezoelectric material as the plurality of transducers.

4. The pMUT of claim 3, wherein the MEMS switch is a capacitive switch comprising a cantilever or fixed beam further comprising the piezoelectric material.

5. The pMUT of claim 3, wherein the plurality of MEMS switches comprises a MEMS switch connected in series with at least one of a drive/sense electrode and a ground electrode of an individual transducer element.

6. The pMUT of claim 5, wherein the plurality of MEMS switches comprises a MEMS switch connected in series with the drive/sense electrode of an individual transducer element, the MEMS switch disposed between the transducer element and a drive/sense channel and operable to selectably pass a drive/sense voltage.

7. The pMUT of claim 1, wherein the array comprises a plurality of transducers having drive/sense electrodes selectably coupled to a first drive/sense channel by the MEMS switches, wherein each of the plurality of MEMS switches is coupled to one or more MEMS switch controllers that are to control states of the MEMS switches to couple an individual transducer to the first drive/sense channel.

8. The pMUT of claim 7, wherein the array further comprises a first column of transducers, each transducer in the first column coupled to a first drive/sense channel through one of first MEMS switches, and wherein states of the first MEMS switches are to couple a first transducer of the first column to the first drive/sense channel at a first time while decoupling all other transducers of the first column from the first drive/sense channel.

9. The pMUT of claim 8, wherein states of the first MEMS switches are to couple a second transducer of the first column to the first drive/sense channel at a second time while decoupling all other transducers of the first column from the first drive/sense channel.

10. The pMUT of claim 9, wherein the array is a two dimensional array further comprising a second column of transducers with individual transducers of the second column aligned into rows with individual transducers in the first column, wherein each transducer in the second column is coupled to a second drive/sense channel through at least one of second MEMS switches, and wherein states of the second MEMS switches are to match the states of the first MEMS switches to couple a first transducer of the second column to the second drive/sense channel at the first time and to couple a second transducer of the second column to the second drive/sense channel at the second time.

11. The pMUT of claim 7, wherein the one or more MEMS switch controllers further comprise additional MEMS switches disposed over a third area of the transducer substrate or CMOS transistors disposed over a CMOS substrate.

12. The pMUT of claim 1, wherein the MEMS switch is connected to a sample and hold circuit connected to a drive/sense electrode of the transducer.

13. The pMUT of claim 12, wherein the sample and hold circuit further comprises a capacitor disposed over the transducer substrate.

14. The pMUT of claim 12, wherein the sample and hold circuit comprises a plurality of MEMS switches connected to a transducer drive/sense channel, each of the MEMS switches further coupled to a capacitive element with the plurality operable to sequentially store a sample of a time varying drive/sense voltage on the channel to one of the capacitors and enable analog beamforming directly at the transducer.

15. An apparatus for generating and sensing pressure waves in a medium, the apparatus comprising:
the pMUT array of claim 1;
one or more signal generator coupled to the pMUT array to apply an electrical drive signal on a first drive/sense channel;
one or more receiver coupled to the pMUT array to receive an electrical response signal from the first drive/sense channel;
one or more switch controller connected to at least a first of the MEMS switches to couple different ones of the piezoelectric transducers to the first drive/sense channel over time; and
at least one signal processor coupled to the receiver to process a plurality of electrical response signals received from the drive/sense channel.

16. The apparatus of claim 15, wherein the pMUT array is a two-dimensional array with a first plurality of transducers along a first dimension coupled to the first drive/sense channel, a second plurality of transducers along the first dimension coupled to a second drive/sense channel, and wherein the first and second plurality of transducers form rows of transducers along a second dimension with the at least one switch controller to set a plurality of switches to a same state coupling all transducers of a same row to the drive/sense channels concurrently.

17. The apparatus of claim 15, wherein the generator is coupled to a first pole of at least a first of the MEMS switches and is to apply an electrical drive signal to cause a transducer connected through a MEMS switch to resonate at frequencies between 1 MHz and 50 MHz.

18. A method of generating and sensing pressure waves in a medium, the method comprising:
coupling a first piezoelectric micromachined transducer (pMUT) of a pMUT array disposed over a transducer substrate to a first drive/sense channel during a first time period by setting a first MEMS switch to a first state while setting a second MEMS switch to a second, complementary, state;
applying an electrical drive signal on the first drive/sense channel during a first portion of the first time period;
receiving an electrical response signal from the first drive/sense channel during a second portion of the first time period; and
coupling a second pMUT of the array to the first drive/sense channel during a second time period by setting the second MEMS switch to the first state while setting the first MEMS switch to the second, complementary, state.

19. The method of claim 18, further comprising:
reapplying the electrical drive signal on the first drive/sense channel during the second time period; and
receiving another electrical response signal from the first drive/sense channel.

20. The method of claim 18, further comprising:
coupling a third pMUT of the array to a second drive/sense channel during the first portion of the first time period by setting a third MEMS switch, also disposed over the transducer substrate, to the first state;
applying an electrical drive signal on the second drive/sense channel during the first portion of the first time period; and
receiving an electrical response signal from the second drive/sense channel during the second portion of the first time period.

21. The method of claim 18, wherein setting the first MEMS switch comprises applying a voltage to an electrode coupled to a piezoelectric member of the MEMS switch sufficient to short circuit or capacitively couple the first pMUT to the first drive/sense channel.

22. The method of claim 18, wherein coupling the first pMUT to the first drive/sense channel further comprises
coupling a drive/sense electrode of the first pMUT to a capacitor by setting the first MEMS switch to the first state; and
discharging the capacitor to the first drive/sense channel.

23. The method of claim 18, wherein setting the first MEMS switch to the first state during the first time period and setting the second MEMS switch to the first state during the second time period comprises scanning a first dimension of the array and wherein at least one of the electrical drive signal applied on the second drive/sense channel during the first portion the first time period or the electrical response single received from the second drive/sense channel during the second portion of the first time period is time delayed relative the corresponding electrical drive or sense signal on the first drive/sense channel to phase the array along a second dimension.

* * * * *